(12) United States Patent
Akeel

(10) Patent No.: US 6,378,190 B2
(45) Date of Patent: Apr. 30, 2002

(54) METHOD FOR STRESS-FREE ASSEMBLY OF COMPONENTS

(75) Inventor: Hadi A. Akeel, Rochester Hills, MI (US)

(73) Assignee: FANUC Robotics North America, Inc., Rochester Hills, MI (US)

( * ) Notice: Subject to any disclaimer, the term of this patent is extended or adjusted under 35 U.S.C. 154(b) by 0 days.

(21) Appl. No.: 09/734,534

(22) Filed: Dec. 11, 2000

Related U.S. Application Data

(62) Division of application No. 09/374,919, filed on Aug. 16, 1999, now abandoned, which is a continuation of application No. 08/613,683, filed on Mar. 11, 1996, now Pat. No. 5,987,726.

(51) Int. Cl.$^7$ .......................... B23Q 17/00; B23P 21/00; C21B 11/02
(52) U.S. Cl. ..................... 29/407.08; 29/407.1; 29/714; 74/490.01
(58) Field of Search .......................... 29/407.08, 407.1, 29/714, 407.01; 74/471 R, 471 XY, 479.01, 490, 490.05, 490.06, 490.07, 490.01; 73/862.044, 862.043

(56) References Cited

U.S. PATENT DOCUMENTS

| | | |
|---|---|---|
| 3,624,886 A | 12/1971 | Powers et al. |
| 3,952,979 A | 4/1976 | Hansen |
| 4,536,690 A | 8/1985 | Belsterling et al. |
| 4,561,176 A | 12/1985 | Leddet |
| 4,589,184 A | 5/1986 | Asano et al. |
| 4,641,819 A | 2/1987 | Poland |
| 4,666,362 A | 5/1987 | Landsbergen et al. |
| 4,736,515 A | 4/1988 | Catena |
| 4,738,387 A | 4/1988 | Janufmann et al. |
| 4,811,891 A | 3/1989 | Yamaoka et al. |
| 4,819,496 A | 4/1989 | Shelef |
| 4,821,408 A | 4/1989 | Speller, Sr. et al. |
| 4,831,316 A | 5/1989 | Ishiguro et al. |
| 4,875,273 A | 10/1989 | Yamamoto |
| 4,876,786 A | 10/1989 | Yamamoto et al. |
| 4,894,901 A | 1/1990 | Soderberg |
| 4,976,582 A | 12/1990 | Clavel |
| 4,988,244 A | 1/1991 | Sheldon et al. |
| 5,028,180 A | 7/1991 | Sheldon et al. |
| 5,053,687 A | 10/1991 | Merlet |
| 5,114,300 A | 5/1992 | Shahinpoor et al. |
| 5,125,149 A | 6/1992 | Inaba et al. |
| 5,156,062 A | 10/1992 | Appleberry |
| 5,239,739 A | 8/1993 | Akeel et al. |
| 5,271,290 A | 12/1993 | Fischer |
| 5,272,805 A | 12/1993 | Akeel et al. |
| 5,354,158 A | 10/1994 | Sheldon et al. |
| 5,388,935 A | 2/1995 | Sheldon |
| 5,401,128 A | 3/1995 | Lindem et al. |
| 5,699,695 A | 12/1997 | Canfield et al. |
| 5,715,729 A | 2/1998 | Toyama et al. |
| 5,787,758 A | 8/1998 | Sheldon |
| 5,931,832 A | 8/1999 | Jensen |
| 6,141,863 A * | 11/2000 | Hara et al. .................. 29/714 |

* cited by examiner

Primary Examiner—S. Thomas Hughes
Assistant Examiner—John C. Hong
(74) Attorney, Agent, or Firm—Howard & Howard

(57) ABSTRACT

An apparatus and a method for compliant positioning of an object during an assembly operation wherein the apparatus includes a base plate, a locator plate for mounting an object such as a clamp or a tool spaced from the base plate and a plurality of linear actuators connected between the base plate the locator plate by universal joints providing six degrees of freedom of movement. According to the apparatus and the method a control is connected to the actuators for selectively moving the locator plate to a predetermined position relative to the base plate for contacting a component to be assembled with an object mounted on the locator plate. Two or more of the actuators can be mechanically coupled to move the locator plate with less than six degrees of freedom. The control is responsive to a force applied to the locator plate through the object during assembly of the component for actuating the linear actuators to change the applied force.

3 Claims, 5 Drawing Sheets

| EXAMPLE | COUPLED ACTUATORS | DEGREES OF FREEDOM | MOVEMENT(S) |
|---------|-------------------|--------------------|-------------|
| A | NONE | 6 | $X, Y, Z, \theta x, \theta y,$ and $\theta z$ |
| B | 35/39 or 40/41 or 34/32 | 5 | $Y, Z, \theta x, \theta y$ and $\theta z$ |
| C | 35/39 and 40/41 | 4 | $Z, \theta x, \theta y,$ and $\theta z$ |
| D | 35/39, 40/41 and 34/42 | 3 | $Z, \theta x$ and $\theta y$ |
| E | ALL | 1 | $Z$ |
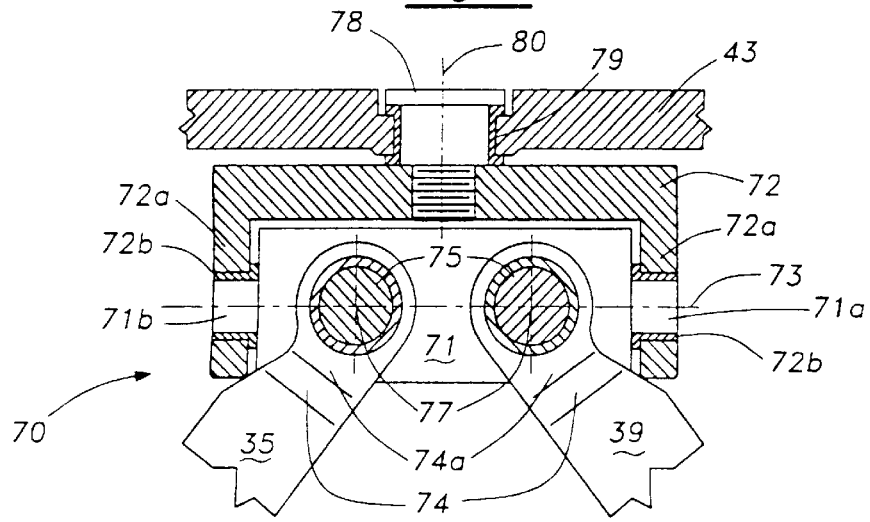
Fig-9
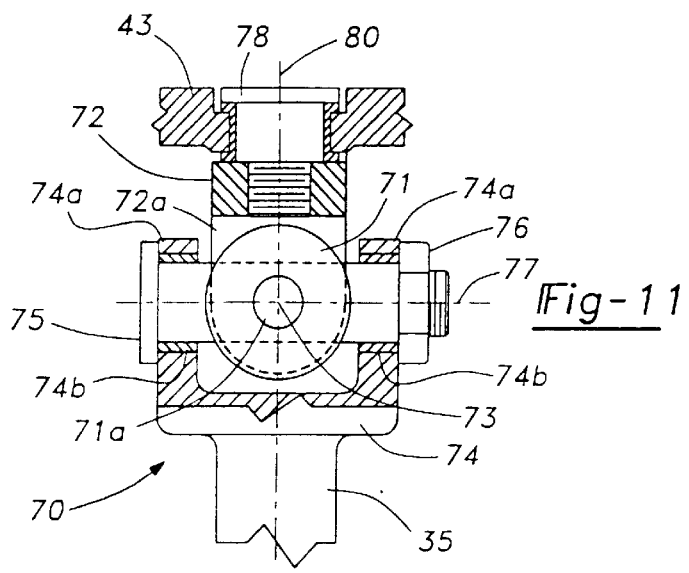
Fig-10
Fig-11

METHOD FOR STRESS-FREE ASSEMBLY OF COMPONENTS

RELATED APPLICATION

This application is a divisional of copending application Ser. No. 09/374,919 filed Aug. 16, 1999, now abandoned which is a continuation of application Ser. No. 08/613,683, filed Mar. 11, 1996 which is now U.S. Pat. No. 5,987,726 which issued Nov. 23, 1999.

BACKGROUND OF THE INVENTION

The present invention relates generally to a method and an apparatus for the flexible assembly of components and subassemblies into an assembly and, in particular, to a method and an apparatus for preventing building stresses into a final assembly.

The process of constructing a vehicle body includes forming subassemblies from individual body panel components, forming larger subassemblies from groups of smaller subassemblies, panels and other components, and forming a final body assembly from the larger subassemblies. During the construction process, the components and subassemblies must be held in fixed, predetermined positions while attachment operations such as welding and inserting fasteners are performed. Typically, the components and subassemblies are held at a work or assembly station in fixtures utilizing locators and clamps which are movable to abut predetermined points on a component surface during the attachment operation and to retract from the surface to permit the subassembly to be moved to another assembly station. Since components are manufactured within a tolerance range, the locations of the predetermined points will vary from component to component and from subassembly to subassembly. The fixtures are often adjusted in holding positions to accommodate the various locations of the predetermined points.

Fixtures for holding components and subassemblies can be classified as "dedicated" or "programmable." A dedicated fixture, also known as "hard automation", is designed to accommodate a single component or subassembly and to perform a specific operation or set of operations. Typically, a dedicated fixture is capable of only clamping and unclamping movements necessary to perform pre-selected operations on the component or subassembly and cannot accommodate a different component or subassembly representing a design change or a different model. In contrast, a programmable fixture is capable of a range of movements. Thus, the programmable fixture can be programmed to execute a pre-determined set of movements to accomodate a particular component or subassembly, and a different set of movements to accomodate another component or subassembly.

Many programmable positioners have mechanisms of the serial type, i.e., each link of the mechanism is serially mounted on the preceding link forming a chain of links. The links may have linear or rotary joints. Mechanisms with linear joints provide higher rigidity but are still appreciably less rigid when compared with conventional hard tooling fixtures. Programmable fixtures of the serial type are described in the U.S. Pat. No. 5,272,805 (see the FIG. 7 and the FIG. 8) which patent is assigned to the assignee of the present invention.

The present invention provides a programmable positioner with a high degree of rigidity as compared with the rigidity of hard tooling fixtures. It realizes its objective by adopting a parallel linkage mechanism formed by a plurality of linear actuators. The rigidity, or stiffness, of the mechanism is determined by the cooperative supporting structure of the parallel linkage wherein the total stiffness of the mechanism is the sum of the stiffening effect of all the links. Mechanisms of this type have been utilized for flight simulators, well known as the "Stewart Platform"—Stewart, The Institute of Mechanical Engineers, Proceedings 1965–1966, pp. 371–394; and for the construction of machine tools as described, for example, in the U.S. Pat. No. 5,354,158 (also, the U.S. Pat. No. 4,988,244 and the U.S. Pat. No. 5,388,935).

One of the most flexible of fixtures is a 6-axis machine tool. A support includes a pair of spaced platforms joined by six powered and extensible legs, which may or may not be crossed, attached to the platforms by universal joints. In one form, the machine tool has an operator, such as a tool in a spindle, mounted on one of the platforms and an object, such as a workpiece, mounted on the other one of the platforms such that the work space is located between the platforms. The length of the legs is individually manipulated to vary the positions of the platforms and, therefore, the object and operator relative to each other.

The U.S. Pat. No. 4,988,244 shows a machine tool having spaced platforms for mounting a tool and a workpiece which platforms are joined by six extensible legs attached to the platforms in three pairs by clevis and trunnion joints. The pairs of legs are crossed and the process operation is performed between the platforms.

The U.S. Pat. No. 5,388,935 shows a machine tool having spaced platforms for mounting a tool and a workpiece which platforms are joined by six extensible legs attached to the platforms by universal joints. At least one of the pairs of legs is crossed and the process operation is performed between the platforms.

The parallel linkage of the above described type of fixture, wherein the process work is done between the two support platforms, is not suitable for work done above the support, such as in assembly operations. The travel restrictions dictated by such a structure are not supportive of flexible assembly wherein the assembly may be performed on relatively large parts that cannot be contained between the two supports. In another type of device, also including a pair of spaced platforms joined by six extensible legs, the tool is mounted on one of the platforms but faces away from the other platform. The object is mounted on a fixture located relative to the one platform. Thus, the other platform serves as a fixed base in order to move the tool toward and away from the object on which an operation is to be performed.

The U.S. Pat. No. 4,536,690 shows a self-propelled robot platform having a support structure which includes a base and a movable tool support joined by six extensible legs wherein the work space is outside the area between the base and the support. Position control feedback utilizes position and velocity sensors.

The U.S. Pat. No. 5,053,687 shows an articulated device having spaced top and bottom plates joined by six extensible link members with a work space outside the area between the plates. The bottom plate fixedly is supported above a base plate. The link members have top ends attached to the top plate in three pairs and bottom ends attached to six slider members by universal joints. The slider members extend through apertures in the bottom plate to engage endless screws mounted on the base plate. Each slider member includes a shock absorber and is connected to position sensor and each link member includes a force sensor. When force is applied to the top plate, the shock absorbers provide passive compliance and a control utilizes the force sensor information in a force return algorithm to calculate corrections to be applied to the position of the top plate.

Whether dedicated or programmable fixtures are utilized, the components or subassemblies are rigidly clamped on the fixtures which are designed for maximum support rigidity. If the process equipment, such as a spot welding gun, is misaligned, it tends to displace the component or components from the desired assembly location. Accordingly, the components may shift relative to each other causing inaccuracy in the assembly, or, the components are caused to stretch or compress against the rigid fixtures before they are permanently welded. Thus, a problem with existing fixtures is that the assemblies are assembled with internal stresses that could cause failure of the assemblies when in use.

SUMMARY OF THE INVENTION

The present invention concerns an apparatus for positioning an object during an assembly operation including a parallel link programmable positioning mechanism having a base plate, a spaced apart locator plate and six linear actuator links extending between the two plates and attached thereto by universal joints. The ends of the actuators are paired in a triangular pattern at each plate and the actuators do not cross one another. Thus, two actuators having one end paired at the base plate each have an opposite end paired with another actuator at the locator plate. The actuators are screw drives for changing the length of each link in a programmable manner. The work space is adjacent the locator plate outside of the space between the plates. When an operation requires corrective action due to high processing forces, the actuators can be of the ball screw type which react to forces applied to the locator plate by backdriving. Rotary position encoders can be utilized to provide motion feedback to a control system which can react to the applied force to increase the holding force for higher support rigidity or decrease the holding force for controlled compliance and a stress free assembly. Also, the actuators can be coupled mechanically to reduce the degrees of freedom and the number of motors and controls required.

In the apparatus, the base plate has an upper surface, the locator plate has upper and lower surfaces and the linear actuators each have a lower end pivotally attached to the upper surface of the base plate and an upper end pivotally attached to the lower surface of the locator plate, the lower and upper ends of each linear actuator being movable relative to one another along a predetermined linear path to move the locator plate relative to the base plate. A plurality of base pivot joints are attached between the upper surface of the base plate and the lower ends of the linear actuators in a generally triangular first pattern, the base pivot joints being arranged in pairs with a midpoint of each base pivot joint pair forming a point of the first pattern. A plurality of locator pivot joints are attached between the lower surface of the locator plate and the upper ends of the linear actuators in a generally triangular second pattern, the locator pivot joints being arranged in pairs with a midpoint of each locator pivot joint pair forming a point of the second pattern.

An object is mounted on the upper surface of the locator plate. The object usually is a clamp for attaching a component to the locator plate or a tool for performing an operation on the component. A control means is connected to the linear actuators for selectively actuating the linear actuators to move the locator plate to a predetermined position relative to the base plate for positioning the object to receive a component to be assembled. A feedback means is coupled to the linear actuators and is connected to the control means. The feedback means is responsive to a force applied to the object during assembly of the component for generating feedback signals representing the applied force to the control means, and the control means is responsive to the feedback signals for actuating the linear actuators to change the applied force. The actuator can be mechanically coupled to coordinate actuation of at least two of the linear actuators to move the locator plate relative to the base plate with less than six degrees of freedom.

The present invention also concerns a method for positioning an object during an assembly operation including the steps of: connecting a base plate to a locator plate with a plurality of linear actuators each having a lower end pivotally attached to the base plate and an upper end pivotally attached to the locator plate; mounting an object on the locator plate; controlling the linear actuators to move the locator plate to a predetermined position relative to the base plate for contacting the object mounted on the locator plate with a component to be assembled; generating feedback signals representing a force applied to the locator plate when the object contacts the component; and actuating the linear actuators to change the applied force in response to the feedback signals. The method can be performed by maintaining the applied force within a predetermined threshold range.

The method according to the present invention also concerns a method for the stress free assembly of sheet metal components on assembly fixtures including at least one programmable fixture having actuators responsive to position control signals from a controller, clamping means for clamping the components to the assembly fixtures and tooling operable on and capable of displacing the components during assembly and generating forces supported by the fixtures. The method includes the steps of: generating control signals from a controller to move at least one actuator and position a fixture at a predetermined location; placing at least two components on the fixture at the predetermined location; clamping the components to the fixture; actuating tooling to assemble the components, the tooling generating forces supported by the fixture and tending to displace the components from the predetermined position; sensing the forces supported by the fixture during actuation of the tooling and generating force signals indicative of a magnitude and direction of the forces; communicating the force signals to the controller; and operating the controller to move the actuator in a direction to reduce the forces below a desirable limit to providing a stress free assembly of the components. The sensing step can be performed by a force sensor measuring at least one of six generalized force components X, Y, Z, $M_x$, $M_y$ and $M_z$ in a generalized cartisian coordinate system, or by a position encoder coupled to the actuator for generating an output signal representing movement of the actuator in response to the applied force.

BRIEF DESCRIPTION OF THE DRAWINGS

The above, as well as other advantages of the present invention, will become readily apparent to those skilled in the art from the following detailed description of a preferred embodiment when considered in the light of the accompanying drawings in which:

FIG. 9 is a table of examples of coupling of the actuators shown in the FIG. 5 based on the movement directions shown in the FIG. 8;

FIG. 10 is a enlarged. fragmentary front elevation view of an alternate embodiment locator pivot joint for the positioner shown in the FIG. 5; and FIG. 11 is a left side elevation view the pivot joint shown in the FIG. 10.

DESCRIPTION OF THE PREFERRED EMBODIMENT

Figure 1:
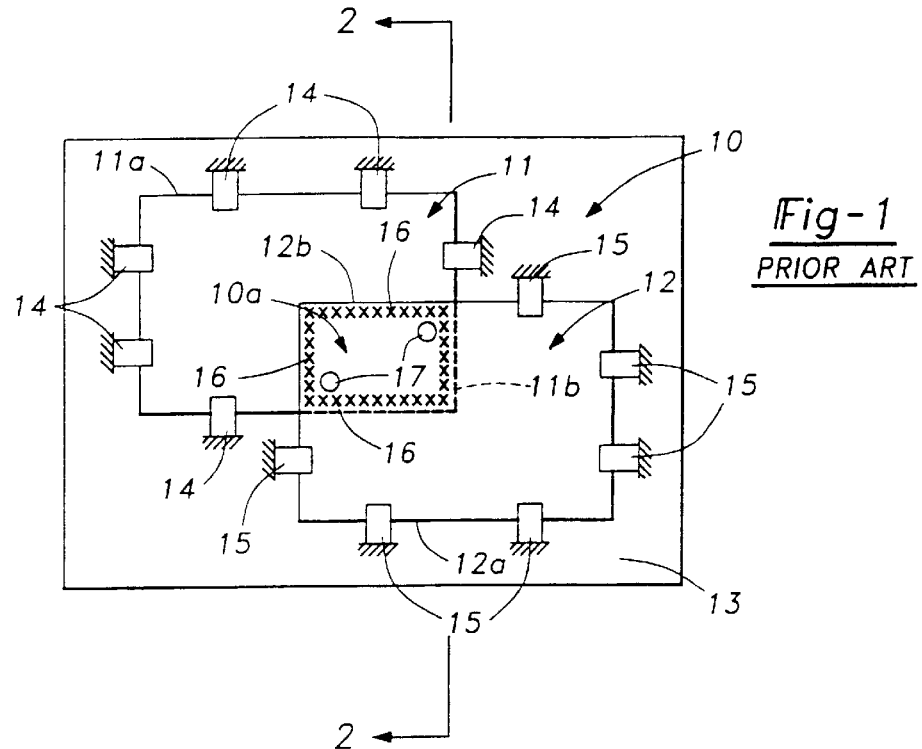
FIG. 1 is a schematic plan view of two components to be assembled together being held in a fixture according to the prior art.
Figure 2:
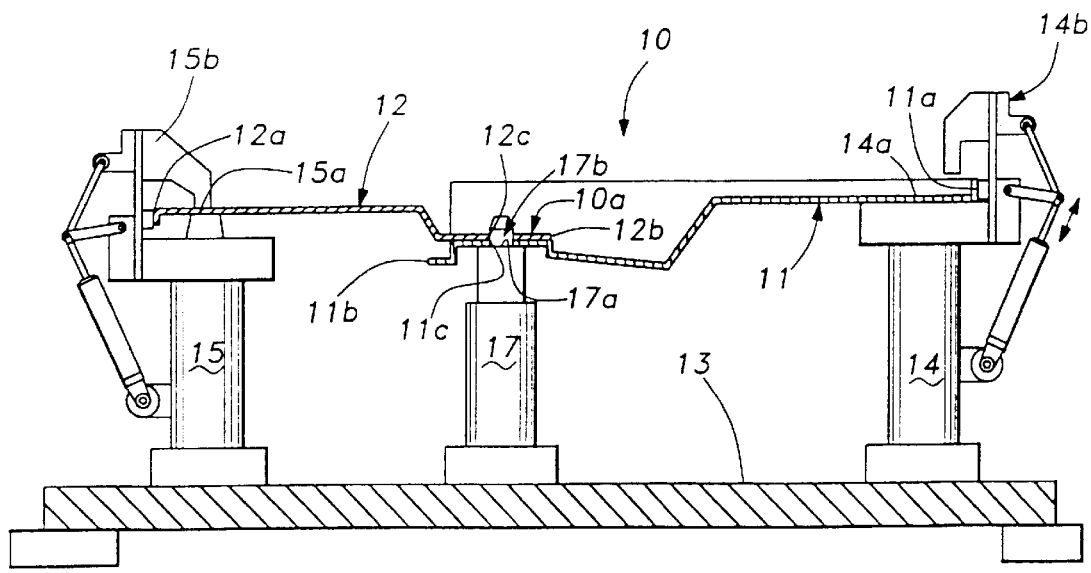
FIG. 2 is a cross-sectional front elevation view of the components and the fixture as if taken along the line 2—2 in the FIG. 1.

As shown in the FIG. 1 and the FIG. 2, an assembly 10 is to be formed from a first component 11 and a second component 12. Although the designations "assembly" and "component" will be utilized in the description of the preferred embodiment of the present invention, the assembly 10 could be a subassembly of a larger assembly and either one or both of the components 11 and 12 could be subassemblies. The FIG. 1 is a schematic plan view of the components 11 and 12 placed on a fixture 13 and the FIG. 2 is a front elevation view of the components and the fixture as if taken along the line 2—2 in the FIG. 1. For the purposes of this example, it is assumed that the components 11 and 12 are each a substantially planar piece of sheet metal which pieces are to be spot welded together with a portion of the component 12 overlapping a portion of the component 11 in the position shown. In accordance with prior art methods of assembly, typically, the first component 11 is placed on the fixture 13 in a first pre-determined position resting on an upwardly facing support surface 14a of each of a first plurality of locators or supports 14. The first component 11 is held in the first pre-determined position against the surfaces 14a by a plurality of clamps 14b which engage a free periphery 11a of the component and each of which is attached to one of the supports 14. The second component 12 is then placed on the fixture 13 in a second pre-determined position resting on an upwardly facing support surface 15a of each of a second plurality of supports 15. The second component 12 is held in the second pre-determined position against the surfaces 15a by a plurality of clamps 15b which engage a free periphery 12a of the component and each of which is attached to one of the supports 15.

The components overlap in an area 10a bounded by an overlapped periphery 11b of the first component 11 and an overlapping periphery 12b of the second component 12. The portions of the components 11 and 12 in the area 10a are to be spot welded together at plurality of points 16. This area 10a rests on an upwardly facing surface 17a of each of a third plurality of supports 17. The first component 11 has a plurality of apertures 11c formed therein and the second component 12 has a plurality of apertures 12c formed therein such that each of the apertures 11c is aligned with one of the apertures 12c. Each of the supports 17 has an upwardly extending tapered locator pin 17b attached thereto which pin extends through an associated pair of the apertures 11c and 12c. Thus, the components are firmly held in the predetermined positions shown by the clamps 14b and 15b and by the pins 17b. The supports 14, 15 and 17 can be any of various types of prior art locators or supports such as those shown in the FIGS. 7 and 8 of the U.S. Pat. No. 5,239,739 which patent is assigned to the assignee of the present invention.

The spot welding process involves the use of spot welding guns that squeeze the components 11 and 12 together as an electric current is applied. This squeezing process is usually associated with lateral forces that attempt to displace the components from their desired positions and are resisted by the supports 14, 15 and 17 holding the free edges 11a and 12a and the overlapping area 10a of the components 11 and 12 respectively. Accordingly, forces build up in the components 11 and 12 depending on the compliance of these components, as well as the compliance of the lateral supports 14 and 15. The lateral supports 14 and 15 are usually made as rigid as possible to prevent the components 11 and 12 from shifting relative to each other causing inaccurate assemblies. However, this high support rigidity gives rise to high loads being applied on the components 11 and 12 and possibly causing their overlapping surfaces to shift relative to each other inside their clamping supports.

Figure 3:
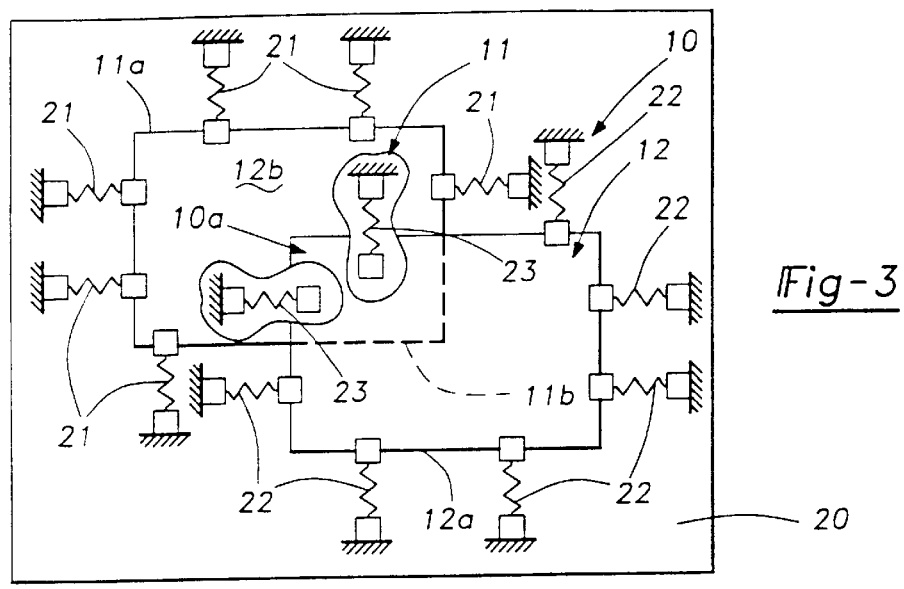
FIG. 3 is a schematic plan view of the two components shown in the FIG. 1 being held in a fixture according to the present invention.

In the FIG. 3, there is shown a fixture 20 having compliant supports in accordance with the present invention. The first component 11 is held in the same first predetermined position along the free edge 11a by a first plurality of compliant supports 21. Similarly, the second component 12 is held in the same second pre-determined position along its free edge 12a by a second plurality of compliant supports 22. The area 10a of the components bounded the overlapped periphery 11b of the first component 11 and the overlapping periphery 12b of the second component 12 rests on a third plurality of compliant supports 23 exposed by cutaway portions of the components. As explained below, the compliant supports 21, 22 and 23 can be selectively controlled to offer relatively high rigidity to accurately position the components to be assembled. When a processing force is applied to the components 11 and 12, the compliant supports 21, 22 and 23 can be controlled to either increase the holding force for even higher support rigidity or reduce the holding force to attain a condition of controlled compliance offering selected resistance to applied forces, hence, minimizing the occurrence and severity of stresses in the final assembly.

In theory, the present invention is based upon the principal of elastic deformation, wherein, for an elastic system, the forces and deflections are related by the equation: $F = K \cdot X$. In the equation, F is the applied force, X is the corresponding deflection and K is a constant that represents the stiffness, or inverse of compliance, of the system. It is obvious that for a given displacement X induced by the process equipment, a relatively rigid system, with a high stiffness constant K, will experience a correspondingly high force F. On the other hand, if the system is provided with compliance, i.e., a low stiffness constant K, the same deflection X will give rise to a correspondingly lower force F. The principal of the present invention builds on this theory by providing fixtures with low stiffness, high compliance supports to prevent the process equipment from inducing high forces as a result of their tendency to displace the components from their clamped positions. The clamping of one component relative to the other, especially at the supports 23, benefits from this compliant mounting since the forces generated by the process equipment are low, thus the clamping forces between the components do not need to be high. Low clamping forces result in low component deformations, low surface marring, and consistent alignment between components, hence, higher assembly accuracy.

A special benefit of the present invention is realized with the growing tendency to use flexible fixturing of automotive components for assembly. Robotic fixtures, comprising robotic devices fitted with clamping devices, are used to locate sheet metal components and clamp them in a desired position. Unlike conventional hard/rigid fixtures used in what is known as "hard automation", robotic fixtures are programmed to adapt to different component configurations, hence, are reusable for a variety of components and provide the basis for flexible automation. Robotic fixtures allow a manufacturing plant to be reconfigured by computer control to produce different product models and sizes without the need to stop production and replace hard fixtures, usually dedicated to one product. A mode of use of robotic fixtures is described in the previously identified U.S. Pat. No. 5,239,739 and the previously identified U.S. Pat. No. 5,272,805.

The present invention addresses a process for the use of robotic fixtures to adjust their resistance to external forces by adjusting their control gain parameters as is well known in servo control techniques. Accordingly, such devices can be programmed to act as a rigid support as the parts are located and clamped relative to each other for accuracy of positioning, then change to low compliance when the process equipment begins exerting its displacing forces on the assembly of components. The assembly then benefits in several ways. The assembly benefits by having a rigid support for positioning whereby the components are located accurately relative to each other. By later adjusting for lower compliance, the process equipment cannot exert high forces, hence, a stress relief assembly is achieved. By utilizing robotic devices, the assembly platform can adapt to components of different sizes and configurations. The compliance can be adjusted selectively to keep some reference locations rigidly positioned while others are allowed to "float," i.e., have low compliance, hence, keeping reference locations common to several components unchanged for high assembly accuracy.

Once clamped by robotic fixtures in the exact relative locations, components can then be processed with process robots, such as spot welding robots. When the process robots engage the components and exert a displacing effect on their location, such robotic fixtures can be programmed to sense the forces applied by the process equipment, reduce their resistance and function in a compliant manner by reducing their control gains, hence, minimizing their resistance to displacement and minimizing their resultant forces. Such an assembly system minimizes the forces applied to the components, hence, their tendency to slip relative to each other. On the other hand, when the process robots approach the components, the components can be located at the accurate positions programmed for the processed robots with no negative impact on the accurate location of the processed targets, such as the location of welding spots.

Figure 4:
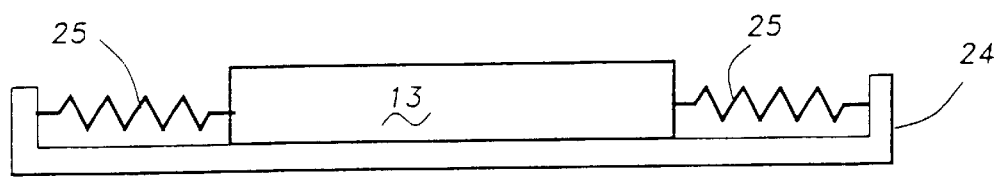
FIG. 4 is a front elevation view of the fixture shown in the FIG. 3 showing an alternate mounting complying with the invention.

The present invention can be practiced together with conventional rigid fixtures now employed in sheet metal assembly plants, such as for automotive body assembly, by changing the mounting arrangement of the fixtures. Instead of mounting the fixtures rigidly on the floor, the fixtures may be provided with compliant supports. The compliance may be built into the fixture supports to be rigid in the vertical plane and compliant in the horizontal plane such that when the components are mounted on the fixtures, the fixtures respond with minimal or no deflection due to the weight of the components as is necessary for the accurate location of the sheet metal components relative to each other for accuracy and assembly. However, when the components are clamped into a clamped assembly in process equipment, such as welding robots which apply displacing forces predominately in the horizontal direction, the overall assembly displaces with low resistance in the horizontal direction, thus relieving the clamped assembly from process forces and displacements. For example, as shown in the FIG. 4, the fixture 13 can be slidably mounted relative to a support structure 24 and compliantly supported laterally by a plurality of compliant supports 25.

Figure 5:
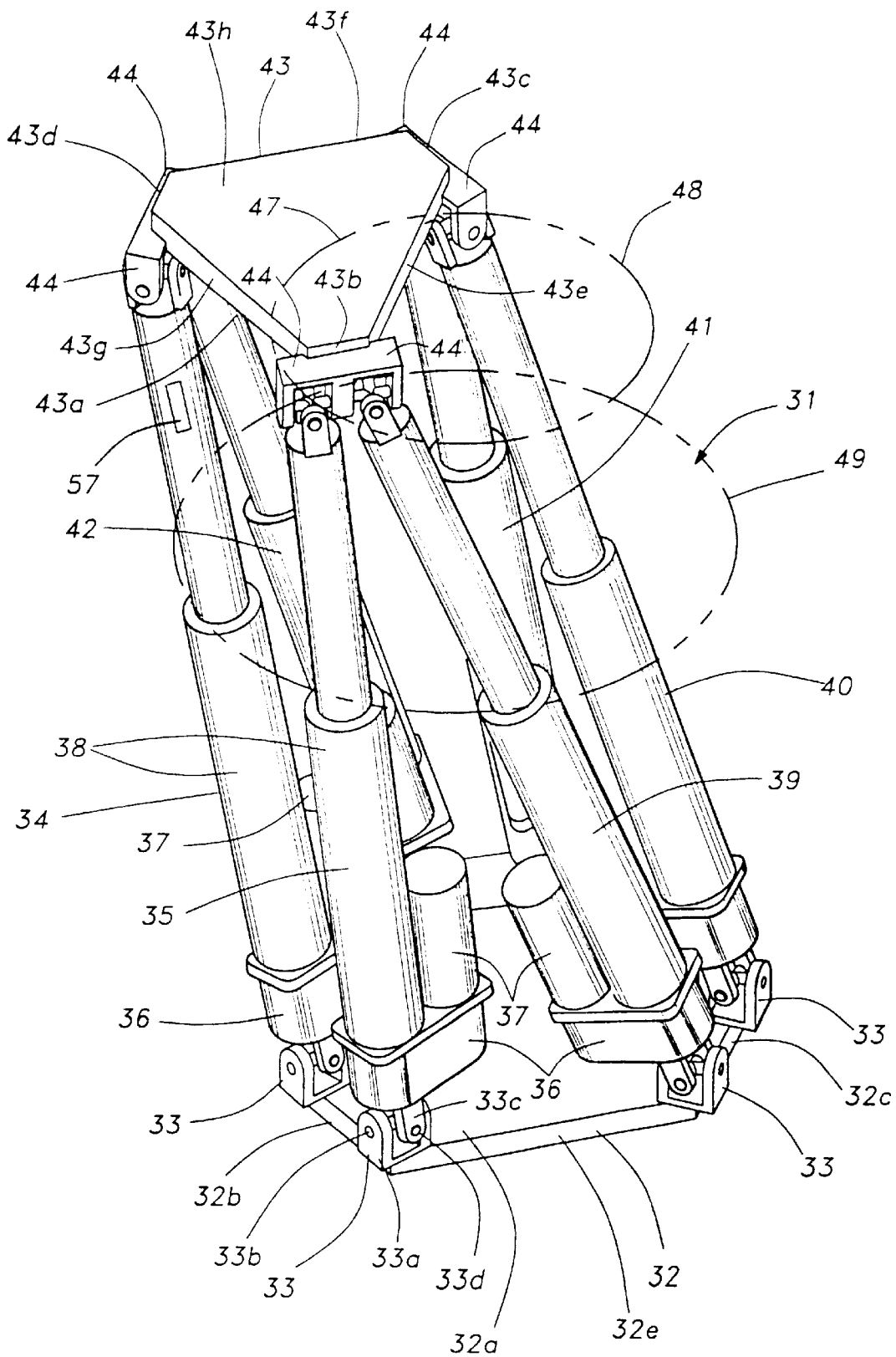
FIG. 5 is a perspective view of a programmable positioner according to the present invention.

There is shown in the FIG. 5 a programmable positioner 31 in accordance with the present invention which can be utilized to create the compliant supports 21, 22 and 23 shown in the FIG. 3 or to create a compliant process tool such as a spot welding robot. The positioner 31 includes a base plate 32 having a generally triangular shape with a generally planar upper surface 32a. The base plate 32 can be fixedly mounted on a suitable support surface, such as a building floor. However, as best shown in the FIG. 6, the points of the triangle are cut off to form three shorter sides 32b, 32c and 32d alternating with three longer sides 32e, 32f and 32g to define six sides of the base plate 32. Mounted at the junction of each one of the shorter sides with one of the adjacent longer sides is one of six base pivot joints 33. Each of the pivot joints 33 has a pair of axes of rotation oriented orthogonally to one another. As best shown in the FIG. 5, the one of the joints 33 mounted at the junction of the sides 32b and 32e has a first generally U-shaped bracket 33a mounted on the upper surface 32a with a pair of upwardly extending spaced legs. Extending between the legs is a first pin 33b having a longitudinal axis which extends in a plane generally parallel to the upper surface 32a and generally perpendicular to the side 32b. The joint 33 also includes a second U-shaped bracket 33c having a pair of downwardly extending spaced legs. A second pin 33d extends between the legs of the second bracket 33c and has a longitudinal axis that extends in the same plane as but transverse to the longitudinal axis of the first pin 33b. The first pin 33b and the second pin 33d are fixed relative to one another, but the first pin is rotatable about its longitudinal axis in the first bracket 33a and the second bracket 33c is rotatable about the longitudinal axis of the second pin 33d. Thus, the base pivot joint 33 has two mutually orthogonal axes of rotation to function as a universal joint.

The joints 33 are each attached to a lower end of a corresponding one of a plurality of linear actuators. A first linear actuator 34 is attached to the joint 33 mounted at the junction of the sides 32b and 32g. A second linear actuator 35 is attached to the joint 33 mounted at the junction of the sides 32b and 32e. The second linear actuator 35 has a gear box 36 attached to the second bracket 33c and a drive motor 37 mounted on the gear box. The gear box 36 is also attached to a lower end of a screw drive 38. The linear actuator 34 has similar components, as do a third linear actuator 39, a fourth linear actuator 40, a fifth linear actuator 41 and a sixth linear actuator 42. The linear actuator 39 is attached to the joint 33 mounted at the junction of sides 32c and 32e, the linear actuator 40 is attached to the joint 33 mounted at the junction of sides 32c and 32f, the linear actuator 41 is attached to the joint 33 mounted at the junction of sides 32d and 32f, and the linear actuator 42 is attached to the joint 33 at the junction of the sides 32d and 32g. The upper end of each of the linear actuators is connected to a locator plate 43. The locator plate 43 is generally triangular in shape, but similarly to the base plate 32, has a generally planer lower surface 43*a* and has the points truncated to form three generally shorter sides 43*b*, 43*c* and 43*d* alternating with three longer sides 43*e*, 43*f* and 43*g*. Mounted at the junction of each of the shorter sides with an adjacent one of the longer sides is one of six locator pivot joints 44. The joints 44 are similar in construction to the joints 33 and are each attached to the upper end of a corresponding one of the linear actuators.

Figure 6:
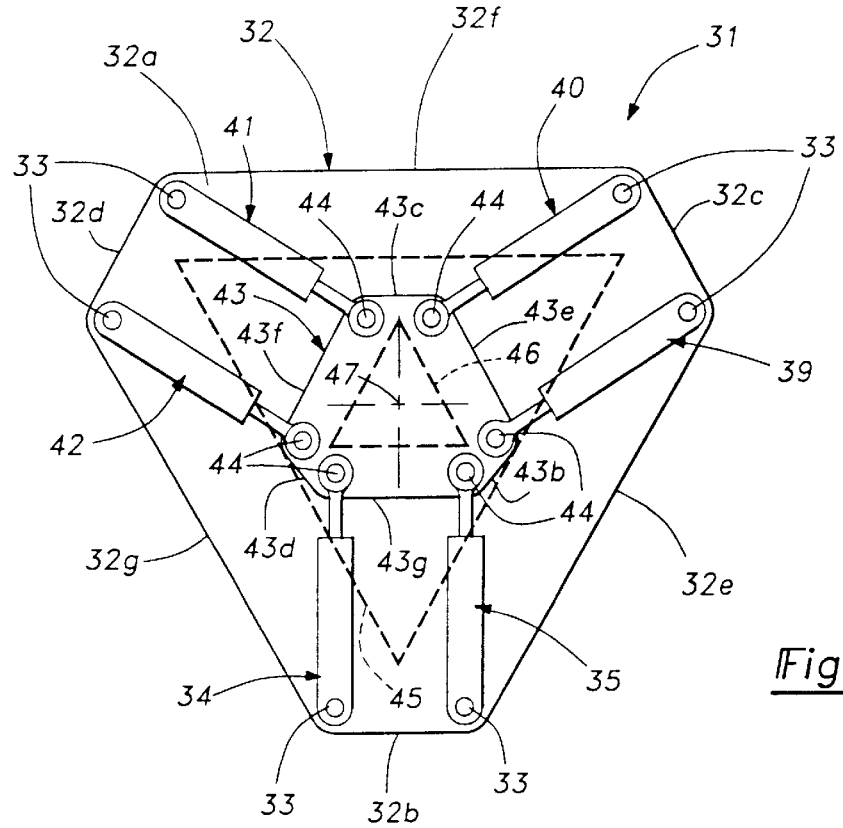
FIG. 6 is a top plan view of the positioner shown in the FIG. 5.

As best shown in the FIG. 6, the locator plate 43 is rotated approximately sixty degrees relative to the base plate 32. The locator plate 43 has a generally planar upper surface 43*h* which can be utilized as a support or mounting surface for objects, such as a body panel clamp or a welding gun, to be used in assembling components such as the panels 11 and 12 shown in the FIG. 1 through the FIG. 3. Thus, the positioner 31 includes the base plate 32, the locator plate 43, six substantially similar linear actuators 34, 35, 39, 40, 41 and 42, the base pivot joints 33 connecting the lower ends of the linear actuators to the base plate, and the locator pivot joints 44 connecting the upper ends of the linear actuators to the locator plate. The pivot joints 33 and 44 are universal joints having two orthogonal intersecting pivotal axes and are arranged in pairs on both bases. The midpoints of each pair of pivot joints 33 form the points of an equilateral triangle 45 on the base plate 32 and the midpoints of each pair of pivot joints 44 form the points of a smaller equilateral triangle 46 on the locator plate 43. The triangles 45 and 46 are oppositely oriented relative to one another. Such a positioner has high rigidity along a generally vertical axis by virtue of the parallel linkages which is critical to the accurate assembly operations required for automotive body assembly wherein the rigidity must be comparable to conventional fixed fixtures of the type shown in the FIG. 1 and the FIG. 2. Lower cost is achieved through the use of similar, relatively inexpensive linear actuators and similar, two axis pivot joints. The positioner according to the present invention also uses an actuator having two links which are free to rotate relative to each other to avoid the costly linear guiding arrangements commonly used in the prior art. The positioner according to the present invention also utilizes a pivot joint having two orthogonal axes which joint is lower in cost and simpler to manufacture and operate than a three orthogonal axes joint commonly known as a spherical joint.

As described below, the programmable positioner 31 utilizes screw drives to change the length of the links in a programmable manner. The screw drives can be low friction ball or sliding-type screws (ACME type). ACME type screws provide a self-locking feature uniquely supportive of automotive assembly operations wherein the support does not react (yield) to the process forces and provides an inherently rigid support. On the other hand, a ball screw type with a brake to prevent back driving when a workpiece is being supported also can be used. The ball type screw can be used when an indication of the process forces may be desirable to provide signals to a control system which can initiate a corrective action to the causes of high process forces. The positioner according to the present invention can utilize rotary position measuring devices (encoders) to indicate the length of the actuators rather than an extensible instrument as in the prior art.

As shown in the FIG. 6, the locator plate 43 has a center or reference point 47 which is spaced equally from the corner points of the triangle 46. The point 47 provides a reference for positioning any object mounted on the locator plate 43. The linear actuators can be controlled to move the point 47 along any desired path limited only by the range of extension of the actuators. For example, through appropriate control of the linear actuators at or near full extension, the point 47 can be moved anywhere in a first area 48 shown as a generally circular first plane in the FIG. 5 with the periphery of the plane being defined by the extension limits of the actuators. As another example, through appropriate control of the linear actuators at partial extension, the point 47 can be moved anywhere in a second area 49 shown in the FIG. 5 as a generally circular, larger diameter second plane.

Figure 7:
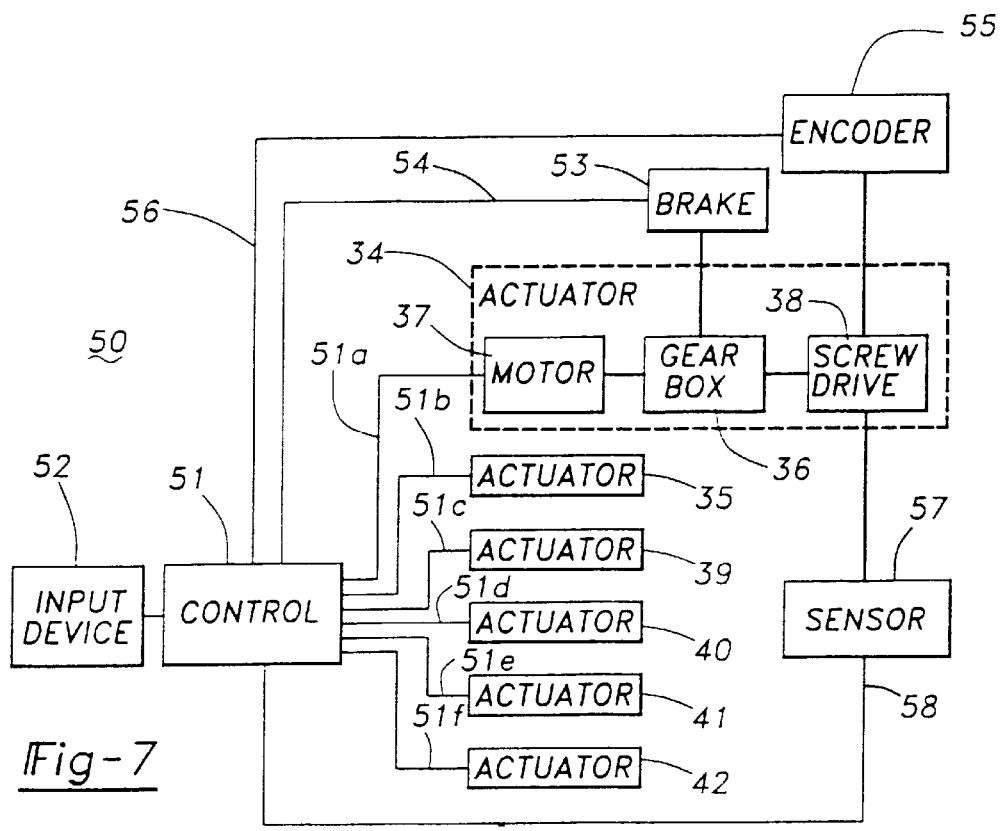
FIG. 7 is a schematic block diagram of a control system for the positioner shown in the FIG. 5.
Figure 8:
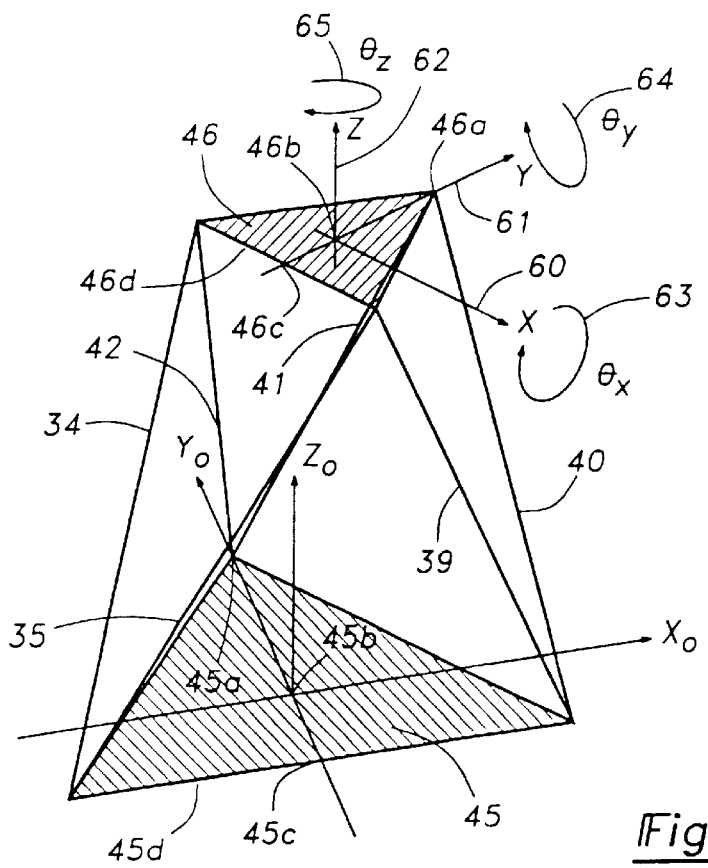
FIG. 8 is a Cartesian coordinate diagram of the directions of movement of the positioner shown in the FIG. 5.

A control system 50 for the six actuators of the positioner 31 is shown in the FIG. 7. A control 51 is connected to an input device 52 for receiving signals to position each of the actuators to effect a desired location for the upper surface 43*h* (see the FIG. 5) of the locator plate 43. The control 51 has a first output connected to a control signal line 51*a* which is connected to the first actuator 34. The line 51*a* is connected to an input of the motor 37 to control the direction and total angle of the rotation and thereby control the length of extension of the screw drive 38 through the gear box 36. In a similar manner, another output of the control 51 is connected by a control signal line 51*b* to the second actuator 35. A third output of the control 51 is connected by a control signal line 51*c* to the third actuator 39, a fourth output is connected by a control signal line 51*d* to the fourth actuator 40, a fifth output is connected by a control signal line 51*e* to the fifth actuator 41 and a sixth output is connected by a control signal line 51*f* to the sixth actuator 42. Typically, the control 51 is a conventional linear actuator control which is responsive to signals representing the desired movement of each actuator for applying electrical power to the actuators. The coordinated movement of the actuators is achieved by utilizing the input device 52 to generate information as to the length of extension of each of the actuators required to achieve a desired final position of the point 47 and the object mounted thereat. The input device 52 can be, for example, a programmed computer which has stored therein equations defining the physical relationship of the locator plate 43 relative to the base plate 32 in terms of the extensions of the linear actuators. A keyboard or a mouse incorporated in the input device 52 can be used to input the required final location for the point 47 and orientation of the surface 43*h* and the computer then calculates the required extension for each of the actuators. The input device 52 then generates the actuator extension information to the control 51 which in turn generates the necessary control signals on the lines 51*a* through 51*f* to extend, retract or leave unchanged each of the linear actuators.

As stated above, the actuators can be of the ball screw type with a brake for preventing back driving. However, if the brake is released, any forces acting in a direction of the axis of extension will tend to back drive the screw. As shown in the FIG. 7, a brake 53 can be mechanically coupled to the gear box 36 of the actuator 34 and can be actuated by a signal on a brake signal line 54 connected between an input of the brake and an output of the control 51. Also, feedback means in the form of an encoder 55 can be mechanically coupled to the screw drive 38 of the actuator 34 to either verify that the actuators have reached their desired extension, or respond to any change in extension, and generate a feedback signal on a feedback signal line 56 connected between an output of the encoder and an input of the control 51. The input device 52 reads the feedback signal representing the deflection X and, knowing the combined stiffness constant K of the positioner 31 including the actuators, the joints, the drive train and the servo controls gain, calculates the applied force F. Now the input device 52 can determine whether to generate a control signal to cause the actuator 34 to extend to increase the rigidity, to make no change thereby maintaining the compliance, or to retract to increase the compliance. Accordingly, the control system 50 can maintain a predetermined amount of compliance whereby the positioner 31 is rigid until a force threshold is reached at which point one of the above discussed actions is implemented which can include adjusting the compliance to maintain the force within a threshold range. The threshold force must be enough to support the component or perform the operation, but lower than a force that can cause excessive internal stresses in the assembly. In addition, the force F can be an indicator of misalignment in the process tool which is applying the force such that the input device 52 can issue a warning message to a worker or even automatically correct the tool support to reduce the misalignment. The encoder 55 can be a linear type device, or a rotary type device where a ball screw type actuator is utilized. Although not shown, each of the six linear actuators can be coupled to an associated brake, such as the brake 53, and an associated encoder such as the encoder 55. However, it is conventional for the motor 37 to include an encoder and brake within the motor frame.

Each of the actuators also can be provided with a single parameter force sensor which senses the magnitude of the longitudinal force experienced by each actuator. For example, a sensor 57 can be mounted on an exterior surface of the actuator 34 as shown in the FIG. 5. The sensor 57 can be of the strain gage type which generates a force proportional sensor signal on a sensor signal line 58 connected between an output of the sensor and an input of the control 51. The control 51 utilizes the force proportional sensor signals in an algorithm that determines the control signals to be generated to retract or extend one or more of the actuators to adjust the compliance of the positioner 31.

While the movement of the actuators is coordinated as a group, each of the actuators can be extended by a different amount to achieve the desired final position for the point 47. Thus, the positioner 31 has six degrees of freedom of movement. Based upon the Cartisian coordinate system, the possible motions of the reference point 47 are defined as linear movement along X, Y and Z axes and rotational movement about the X, Y and Z axes. Accordingly, a force sensor can be utilized to measure any one of six generalized force components in a generalized Cartesian coordinate system; linear forces along the X, Y and Z axes, and moments $M_x$, $M_y$ and $M_z$ about those axes. As shown in the FIG. 8, a set of fixed inertial axes identified as $X_0$, $Y_0$ and $Z_0$ are associated with the triangle 45 of the base plate 32 to define the location and orientation of the locator plate 43, represented by the triangle 46, relative to a fixed reference. The $Y_0$ axis extends through a midpoint between the lower ends of the actuators 41 and 42, marked by a first point 45a of the base plate triangle 45, through a junction 45b of the reference axes and through a midpoint 45c of a first side 45d of the base plate triangle opposite the first point. The junction 45b corresponds to the central point of the triangle 45. The $X_0$ axis extends through the junction 45b generally parallel to the first side 45d. The $Z_0$ axis extends through the junction 45b perpendicular to the plane of the base plate triangle 45. The axes identified as X, Y and Z are associated with the triangle 46 of the locator plate 43. The Y axis extends through a midpoint between the upper ends of the actuators 40 and 41, marked by a first point 46a of the locator plate triangle 46, through a junction 46b of the reference axes and through a midpoint 46c of a first side 46d of the locator plate triangle opposite the first point. The X axis extends through the junction 46b generally parallel to the first side 46d. The Z axis extends through the junction 46b perpendicular to the plane of the locator plate triangle 46. The junction 46b corresponds to the center or reference point 47 shown in the FIG. 5 and the FIG. 6. Movements of the locator plate 43 along the X, Y and Z axes are designated by arrows 60, 61 and 62 respectively. The arrows 60 and 61 represent movement relative to the $X_0$ and $Y_0$ reference axes respectively. The arrow 62 represents movement relative to the $Z_0$ reference axis. Movements about the X, Y and Z axes, through angles $\theta_x$, $\theta_y$ and $\theta_z$ respectively, are designated by arrows 63, 64 and 65 respectively.

However, if fewer than six degrees of freedom are required, by mechanically coupling the actuators to move in dependent groups, the number of degrees of freedom can be reduced and fewer motors and control signals need to be used. There is shown in the FIG. 9 a table of various examples representing possible combinations of actuators coupled for synchronous movement and the resultant degrees of freedom. Actuators for which movement is to be synchronized can be controlled by the control 51 or, can be mechanically coupled such that only a single motor is required for each group of actuators to be moved synchronously. For example, one of the motors 37 shown in the FIG. 7, such as the motor of the actuator 34, can be coupled to also drive one or more of the other actuators through gears (not shown) or by V-belts (not shown) thereby eliminating the motors coupled to these other commonly driven actuators. Also, coupling certain actuators may dictate that other actuators be coupled or controlled simultaneously since the ends of the actuators at both the base plate 32 and the locator plate 43 remain fixed relative to each other.

In an example A shown in the FIG. 9, none of the six actuators are coupled for synchronous movement and the positioner 31 has six degrees of freedom. In an example B, the actuators 35 and 39 are coupled to move in unison. Since the actuators 35 and 39 have upper ends equally spaced on opposite sides of a first point 46a of the locator plate triangle 46 and lower ends equally spaced on opposite sides of the midpoint 45e, movement of the point 46a is confined within the $Y_0$–$Z_0$ plane with no movement in the $X_0$ direction thereby producing five degrees of freedom. Although the point 47 may experience movement in the $X_0$ direction, such movement would be coupled to either the $Y_0$ or the $Z_0$ movement to be still limited to five degrees of freedom. Other such combinations of paired actuators producing five degrees of freedom are the actuators 40 and 41, or the actuators 42 and 34. In an example C, two pairs of coupled actuators on opposite sides of the X and Y axes, such as the actuators 35 and 39 coupled and the actuators 40 and 41 coupled, prevent movement along the X and Y axes to produce four degrees of freedom.

In an example D, three pairs of coupled actuators, such as the actuators 35 and 39 coupled, the actuators 40 and 41 coupled and the actuators 34 and 42 coupled, to prevent movement along the X and Y axes and rotation about the Z axis to produce three degrees of freedom. In an example E, if all of the actuators are coupled together, the positioner 31 has only one degree of freedom since it can move the locator plate 43 only up and down in the Z axis direction.

There is shown in the FIG. 10 and the FIG. 11 and alternate embodiment locator pivot joint 70 which can be substituted for the locator pivot joints 44 connecting the locator plate 43 with the upper ends of the actuators 34, 35, 39, 40, 41 and 42. The pivot joint 70 includes a generally cylindrical body 71 having a pair of axle extensions 71a extending from opposite ends thereof. The axle extensions 71a are rotatably received in apertures formed in a pair of legs 72a of an inverted generally U-shaped bracket 72. The axle extensions 71a can be retained in bearings 72b, which can be any suitable type such as a bushing or a roller bearing, retained in the apertures in the legs 72a. Thus, the body 71 is free to rotate about a longitudinal axis 73 extending between the apertures in the legs 72a.

The upper ends of the actuators 35 and 39, for example, each have a generally U-shaped bracket 74 attached thereto which brackets each have a pair of legs 74a positioned on opposite sides of the body 71. A pair of spaced apart pins 75 extend through apertures formed in the body 71 transverse to the longitudinal axis 73 and each of the pins 75 also extends through apertures formed in the pair of legs 74a of an associated one of the brackets 74. The pins 75 can have an enlarged head and be threaded at an opposite end for retaining a nut 76. The pins 75 can extend through bearings 74b, which can be any suitable type, which bearings are retained in the apertures in the legs 74a. Thus, the upper ends of the actuators 35 and 39 are free to rotate about a longitudinal axis 77 of the associated one of the pins 75.

The bracket 72 is rotatably attached to the locator plate 43 by a pin 78 extending through an aperture formed in the locator plate. The pin 78 has an enlarged head and an opposite threaded end engaging the bracket 72 between the legs 72a. The pin 78 can extend through a bearing 79 retained in the aperture in the locator plate 43 and has a longitudinal axis 80 about which the bracket 72 can rotate. Thus, the locator pivot joint 70 has two universal joints constrained to swivel in unison about the axis 73 of the body 71 and the axis 80 of the pin 78, and to swivel independently about the axes 77 of the pins 75 for a combination of four degrees of freedom. The alternate embodiment joints 70 are comparably less expensive than a pair of conventional three orthogonal axes joints.

In all of these examples, the parameters X, Y, Z, $\theta_x$, $\theta_y$ and $\theta_z$ describe the motion of the center point 47 of the locator plate 43 relative to the base coordinate system $X_0$, $Y_0$ and $Z_0$. It is recognized that by virtue of the parallel linkage mechanism, strong coupling may exist among different coordinates and that independent motions of less than six degrees of freedom may prevail at a point other than the center point 47 of the locator plate 43.

In accordance with the provisions of the patent statutes, the present invention has been described in what is considered to represent its preferred embodiment. However, it should be noted that the invention can be practiced otherwise than as specifically illustrated and described without departing from its spirit or scope.

What is claimed is:

1. A method for stress free assembly of sheet metal components on assembly fixtures including at least one programmable fixture having actuators responsvie to position control signals from a controller, clamping means for clamping the components to the assembly fixtures and tooling operable on and capable of displacing the components during assembly and generating forces supported by the fixtures, comprising the steps of:

a. generating control signals from a controller to move at least one actuator and position a fixture at a predetermined location;

b. placing at least two components on the fixture at the predetermined location;

c. clamping the components to the fixture;

d. actuating tooling to assemble the components, the tooling generating forces supported by the fixture and tending to displace the components from the predetermined position;

e. sensing the forces supported by the fixture during actuation of the tooling and generating force signals indicative of a magnitude and direction of the forces;

f. communicating the force signals to the controller; and g. operating the controller to move the actuator in a direction to reduce the forces below a desirable limit to providing a stress free assembly of the components.

2. The method according to claim 1 wherein the step e. is performed by a force sensor measuring at least one of six generalized force components $X, Y, Z, M_x, M_y$ AND $M_z$ in a generalized cartisian coordinate system.

3. The method according to claim 1 wherein the step e. is performed by a position encoder coupled to the actuator for generating an output signal representing movement of the actuator in response to the forces.

* * * * *